United States Patent [19]

Wagnières et al.

[11] Patent Number: 5,054,867
[45] Date of Patent: Oct. 8, 1991

[54] APPARATUS FOR IRRADIATING THE BRONCHI OF A PATIENT FOR THE PURPOSE OF PHOTODYNAMIC THERAPY

[75] Inventors: Georges Wagnières, Lutry; Hubert van den Bergh, Goumoens-la-Ville; Philippe Monnier, Lausanne, all of Switzerland

[73] Assignee: Ciba-Geigy Corporation, Ardsley, N.Y.

[21] Appl. No.: 638,254

[22] Filed: Jan. 4, 1991

[30] Foreign Application Priority Data

Jan. 9, 1990 [CH] Switzerland ............................ 58/905

[51] Int. Cl.$^5$ ............................................. G02B 23/26
[52] U.S. Cl. ......................................... 385/31; 128/4; 128/6
[58] Field of Search ................. 350/96.1, 96.23; 128/4, 128/6

[56] References Cited

U.S. PATENT DOCUMENTS

| | | |
|---|---|---|
| 4,017,150 | 4/1977 | Imai . |
| 4,551,129 | 11/1985 | Coleman et al. . |
| 4,660,925 | 4/1987 | McCaughan, Jr. .......... 350/96.10 X |
| 4,693,244 | 9/1987 | Daikuzoni ....................... 128/303.1 |
| 4,693,556 | 9/1987 | McCaughan, Jr. .......... 350/96.10 X |
| 4,927,231 | 5/1990 | Levatter ........................... 350/96.32 |

Primary Examiner—John D. Lee
Assistant Examiner—Stephen W. Barns
Attorney, Agent, or Firm—Harry Falber

[57] ABSTRACT

An apparatus for irradiating the bronchi of a patient for the purpose of photodynamic therapy has an optical fibre (11) that feeds the light of a laser into a bronchoscope and is surrounded by a light-guide tube (8) and an outer tube (2). The distal end (13) of the optical fibre (11) is embedded in a silicone composition (17) containing 7 parts per thousand of TiO$_2$ particles having a particle size of 0.2 μm. The silicone composition (17) fills the front end of the light-guide tube (8) as far as the end face (6) of an aluminium cylinder (5) which acts as a mirror. The light dispersed by the TiO$_2$ particles is emitted radially through the light-guide tube (8) and the front portion of the outer tube (2) and acts on the patient's bronchi.

10 Claims, 1 Drawing Sheet

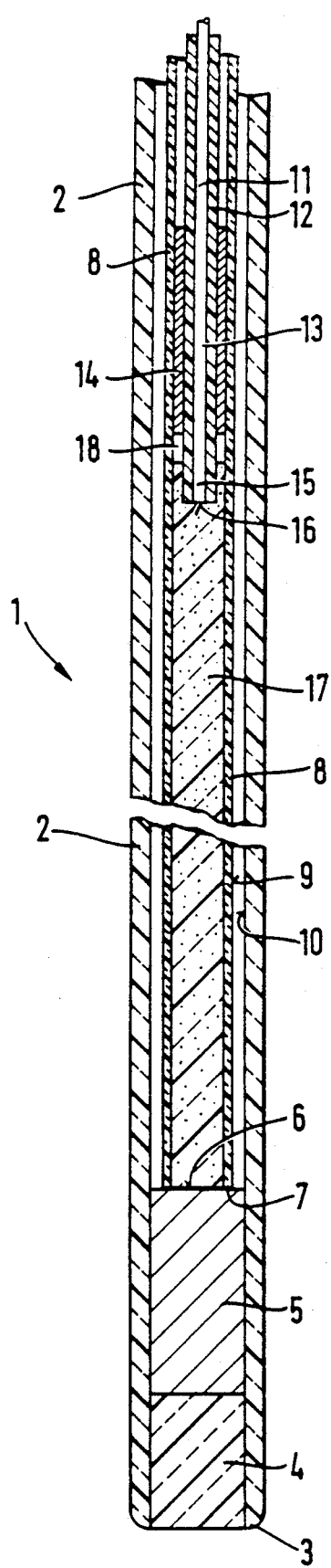

APPARATUS FOR IRRADIATING THE BRONCHI OF A PATIENT FOR THE PURPOSE OF PHOTODYNAMIC THERAPY

The invention relates to an apparatus for irradiating the bronchi of a patient for the purpose of photodynamic therapy, which apparatus has an optical fibre that feeds the light of a laser into a bronchoscope.

A bronchoscope of that type is described in Chemistry in Britain, Vol. 22, No. 5, May 1986, Hubert van den Bergh, "Light and porphyrins in cancer therapy" and permits the detection and treatment of malignant lung tumours, especially on the furcate branches of the bronchi. Such treatment involves injecting a patient with porphyrin. After several days, the tumor tissue has absorbed considerably more of the dyestuff than has the healthy tissue. If the suspicious site is then irradiated, for example with a UV krypton laser at approximately 410 nm, which laser is connected to a quartz-fibre optical system, the cancer tissue is recognized by the red light emanating therefrom. In addition to this effect, which permits the detection of tumours, porphyrin has yet another advantageous property which is that it absorbs red light strongly, there being triggered in the diseased tissue a series of photochemical reactions which kill the tumour tissue, which contains the higher levels of porphyrin. The red light required for that purpose can be conveyed to the tumour likewise by way of a quartz-fibre optical system, thereby selectively destroying the cancer in the course of such photodynamic therapy. The apparatus described in connection with FIG. 3 of the above-mentioned publication makes it possible to irradiate only a tumour lying in front of the end of the fibre. FIGS. 8 and 9 show an apparatus for irradiating the oesophagus, which apparatus permits the radial diffusion of the axially incident light. A Teflon tube filled with an epoxy resin is used for that purpose, the face of the end of the fibre being arranged at an axial distance from the epoxy resin composition, which contains $TiO_2$ particles.

Another apparatus for irradiating the oesophagus is known from U.S. Pat. No. 4,660,925. In that apparatus, the fibre core, which is bared at the light-emitting end, is embedded in a dispersing medium which is itself surrounded by a tube-like transparent protective sheath. The light-emitting end of the fibre core, however, projects by a great distance into the dispersing medium surrounded by the protective sheath so that the radial radiation of the light is restricted to a small area in relation to the dimensions of the tube-like protective sheath. In addition, the diameter of this protective sheath is considerably greater than the diameter of the fibre so that, when the apparatus is passed through the biopsy channel of a bronchoscope, difficulties may occur that are caused by the geometrical dimensions of this apparatus.

Proceeding from that prior art, the problem of the invention is to provide an apparatus of the type mentioned at the beginning that is sufficiently small to be introduced into the bronchi, and that diffuses radially the light fed in by way of the fibre, with the smallest possible losses, even after a relatively long period of use.

This problem is solved according to the invention in that the fibre is surrounded by a light-guide tube which projects beyond the light-emitting face of the end of the fibre by many times the fibre's diameter, and the end of the fibre is embedded in a silicone composition that contains $TiO_2$ powder and that extends from the end of the fibre to the end of the light-guide tube.

Such an arrangement provides not only the possibility of miniaturisation but also, by reason of the high degree of transparency of silicone, a high degree of efficiency as well as a high degree of ageing stability since the silicone retains its good optical properties for a very long period.

In a preferred embodiment, the end of the fibre is fixed in position in the light-guide tube by a centring cylinder. Between the centring cylinder and the silicone composition and in the vicinity of the end face there is arranged an annular gap which extends round the optical fibre and is delimited radially by the light-guide tube. The light-guide tube consists preferably of PTFE and is preferably surrounded by an outer tube that is immovable in the axial direction with respect thereto and that projects beyond the distal end of the light-guide tube, there being arranged in the projecting portion an aluminium cylinder which acts as a mirror and a PTFE cylinder which acts as a closing plug.

There is an open annular space between the light-guide tube and the outer tube. The light-guide tube projects by approximately 3 cm beyond the end of the fibre and forms a diffuser in that portion. For that purpose, the silicone composition is preferably mixed with 7 parts per thousand of $TiO_2$ powder having a particle size of 0.2 micrometer.

In one embodiment of the invention, the light-guide tube has an inside diameter of only 0.8 mm and an outside diameter of approximately 1.1 nm. The outer tube then has an inside diameter 1.4 mm and an outside diameter of 1.9 mm.

An embodiment of the invention is described in detail hereinafter with reference to the drawing. The single FIGURE shows the front end of an apparatus according to the invention that can be introduced into the biopsy channel of a bronchoscope.

The drawing shows a bronchial light diffuser indicated generally by the reference numeral 1. The bronchial light diffuser 1 has such a small diameter that it fits through the biopsy channel of a bronchoscope.

The bronchial light diffuser 1 comprises an outer tube 2 of PTFE (Teflon) having an inside diameter of 1.4 mm and a wall thickness of 0.25 mm. The outer tube 2 extends from the distal end 3, shown at the foot of the drawing to a distance that is greater by a suitable length than the length of the bronchoscope to be used. The outer tube 2 is closed at the distal surface to the inner surface of the outer tube 2.

An aluminimu cylinder 5, of which the end face 6 facing away from the distal end 3 is in the form of a mirror, rests against the end face, facing away from the distal end 3, of the Teflon plug 4.

Resting against the end face 6 is the distal end 7 of a light-guide tube 8 of PTFE which extends through the outer tube 2, an annular gap being present between the outer surface 9 of the light-guide tube 8 and the inner surface 10 of the outer tube 2. The light-guide tube 8 has an outside diameter of approximately 1.1 mm while the outer tube 2 has an inside diameter of 1.4 mm and an outside diameter of 1.9 mm.

As shown in the upper portion of the drawing, an optical fibre 11 surrounded by a cladding 12 projects into the light-guide tube 8. The optical fibre 11 has a core diameter of 200 $\mu$m and a cladding diameter of 280

μm. The numerical aperture of the optical fibre is preferably 0.21.

The distal end 13 of the optical fibre 11 is secured inside a brass centring cylinder 14 which is in turn adhesively bonded in the light-guide tube 8 so that it cannot be moved in the axial direction. The fibre end 15 in the immediate vicinity of the light-emitting face 16 projects slightly out of the centring cylinder 14 and is embedded in a silicone composition 17 in such a manner that an annular gap 18 filled with air is present between the centring cylinder 14 and the silicone composition 17.

The silicone composition 17 fills the space between the end face 6 of the aluminium cylinder 5 and the annular gap 18. It is distinguished by a high degree of transparency and does not turn yellow in the course of time. In order that the light emitted substantially axially from the end face 16 of the optical fibre 11 can be deflected in the radial direction onto the bronchial walls, the silicone composition contains dispersing particles. There particles consist of a titanium oxide powder, which is mixed in with the silicone composition 17. The silicone preferably contains 7 parts per thousand of $TiO_2$ having a particle size of 0.2 μm.

In a preferred embodiment, the concentration of the $TiO_2$ particles in the silicone composition 17 is greater in the region of the axial ends of the silicone composition 17 filling the light-guide tube 8 than in is in the central region. That brings about a greater intensity of the light dispersed radially in the vicinity of the face 16 of the fibre end 15 and int he vicinity of the end face 6 of the aluminium cylinder 5.

A bronchial light diffuser emitting light radially over 360 degrees and having a length of approximately 3 cm is thus formed, which diffuser, owing to its very small diameter, can be introduced even into very narrow bronchi.

It, instead of light emission over 360 degrees, an angle of irradiation of, for example, 180 degrees is desired, the inside of the outer tube 2 can be provided with a reflective metal coating that extends in the shape of a trough over half the circumference of the surface.

What is claimed is:

1. An apparatus for irradiating the bronchi of a patient for the purpose of photodynamic therapy, which apparatus has an optical fibre that feeds the light of a laser into a bronchoscope. wherein the fibre (11) is surrounded by a light-guide tube (8) which projects beyond the light-emitting fact (16) of the end (15) of the fibre by many times the fibre's diameter, and the end (15) of the fibre is embedded in a silicone composition (17) that contains $TiO_2$ powder and that extends from the end (15) of the fibre tot he end (7) of the light-guide tube.

2. An apparatus according to claim 1. wherein the end (13, 15) of the fibre is fixed in position in the light-guide tube (8) by a centring cylinder (14), and an annular gap (18) that extends round the optical fibre (11) in the vicinity of the end face (16) and is delimited radially by the light-guide tube (8) is provided between the centring cylinder (14) and the silicone composition (17).

3. An apparatus according to claim 1. wherein the light-guide tube (8) consists of PTFE.

4. An apparatus according to claim 1, wherein the light-guide tube (8) is surrounded by an outer tube (2) that is immovable in the axial direction and that projects beyond the distal end (7) of the light-guide tube (8), and an aluminium cylinder (5) which acts as a mirror and a PTFE cylinder (4) which acts as a closing plug are arranged in the projecting portion.

5. An apparatus according to claim 4, wherein an open annular space is present between the light-guide tube (8) and the outer tube (2).

6. An apparatus according to claim 4, wherein the outer tube (2) consists of PTFE and has an inside diameter of 1.4 mm and an outside diameter of 1.9 mm.

7. An apparatus according to claim 4, wherein the concentration of the $TiO_2$ powder is lower in the axially central region than it is in the vicinity of the end faces (6, 16) of the optical fibre (11) and the aluminium cylinder (5).

8. An apparatus according to claim 1, wherein the light-guide tube (8) projects by approximately 3 cm beyond the end (13, 15, 16) of the fibre.

9. An apparatus according to claim 1, wherein the silicone composition (17) contains seven parts per thousand of $TiO_2$ powder having a particle size of 0.2 μm.

10. An apparatus according to claim 1, wherein the light-guide tube (8) has an inside diameter of 0.8 mm and an outside diameter of approximately 1.1 mm.

* * * * *